(12) United States Patent
Salerno

(10) Patent No.: US 10,828,469 B2
(45) Date of Patent: Nov. 10, 2020

(54) ASSIST DEVICE FOR SCLEROSING TREATMENT OF VARICOSE VEINS

(71) Applicant: I-VASC S.R.L., Milan (IT)

(72) Inventor: Mario Salerno, Sesto-San Giovanni (IT)

(73) Assignee: I-VASC S.R.L., Milan (IT)

(*) Notice: Subject to any disclaimer, the term of this patent is extended or adjusted under 35 U.S.C. 154(b) by 52 days.

(21) Appl. No.: 15/915,912

(22) Filed: Mar. 8, 2018

(65) Prior Publication Data

US 2018/0193610 A1 Jul. 12, 2018

Related U.S. Application Data

(62) Division of application No. 15/052,470, filed on Feb. 24, 2016, now Pat. No. 9,943,669, which is a division
(Continued)

(30) Foreign Application Priority Data

Dec. 5, 2006 (IT) .............................. MI2006A2333

(51) Int. Cl.
*A61M 25/00* (2006.01)
*A61M 25/10* (2013.01)
*A61B 17/12* (2006.01)

(52) U.S. Cl.
CPC ... *A61M 25/1011* (2013.01); *A61B 17/12045* (2013.01); *A61B 17/12109* (2013.01);
(Continued)

(58) Field of Classification Search
CPC ...... A61M 2025/1052; A61M 25/1011; A61M 25/104; A61M 25/1002; A61M 25/10;
(Continued)

(56) References Cited

U.S. PATENT DOCUMENTS 2,499,045 A 2/1950 Walker et al.
2,984,241 A 5/1961 Carlson
(Continued)

FOREIGN PATENT DOCUMENTS

WO 03/065872 A2 8/2003

OTHER PUBLICATIONS

PCT International Search Report for PCT/EP2007/063320 filed on Apr. 12, 2007 in the name of Mario Salerno.
(Continued)

*Primary Examiner* — William R Carpenter
(74) *Attorney, Agent, or Firm* — Merchant & Gould P.C.

(57) ABSTRACT

Assist device (10) for sclerosing treatment of varicose veins, aimed at being partially inserted into a blood vessel (20), including a tubular element (11), which has at least three ways (13, 14, 15), at least two of which (13, 14) are connected to at least one related inflatable balloon element (12, 12', 16) by at least one through hole (30, 31), and at least one remaining way (15) of said three ways (13, 14, 15) has at least one hole (32) for the passage of a sclerosing substance (17), aimed at reaching a wall (18) of said blood vessel (20), in which at least one (16) of said at least two balloon elements (12, 12', 16) has an elongated shape extending toward at least another balloon element (12, 12') and a volume comprised in the range of 30% to 99% of the space inside said blood vessel.

6 Claims, 3 Drawing Sheets

Related U.S. Application Data of application No. 12/517,695, filed as application No. PCT/EP2007/063320 on Dec. 4, 2007, now Pat. No. 9,302,081.

(52) U.S. Cl.
CPC .. *A61B 17/12136* (2013.01); *A61B 17/12186* (2013.01); *A61M 25/1002* (2013.01); *A61B 2017/12127* (2013.01); *A61M 2025/105* (2013.01); *A61M 2025/1052* (2013.01)

(58) Field of Classification Search
CPC .. A61M 2025/1059; A61M 2025/1095; A61M 2025/1013; A61M 2025/1097; A61M 2025/1047; A61M 2025/1061; A61M 25/007; A61M 25/1006; A61M 2025/1015; A61F 2/958; A61B 17/12136; A61B 17/12022; A61B 2017/2206
See application file for complete search history.

(56) References Cited

U.S. PATENT DOCUMENTS

| | | | | |
|---|---|---|---|---|
| 4,327,736 | A | 5/1982 | Inoue | |
| 4,423,725 | A | 1/1984 | Baran et al. | |
| 4,636,195 | A * | 1/1987 | Wolinsky | A61B 17/22 604/101.03 |
| 4,824,436 | A * | 4/1989 | Wolinsky | A61B 17/22 604/101.03 |
| 5,019,042 | A | 5/1991 | Sahota | |
| 5,090,957 | A | 2/1992 | Moutafis et al. | |
| 5,286,254 | A * | 2/1994 | Shapland | A61M 25/104 604/103.01 |
| 5,405,322 | A * | 4/1995 | Lennox | A61B 17/0057 604/101.01 |
| 5,415,636 | A * | 5/1995 | Forman | A61M 25/104 604/101.03 |
| 5,419,763 | A * | 5/1995 | Hildebrand | A61M 25/1011 604/101.03 |
| 5,439,446 | A * | 8/1995 | Barry | A61F 2/958 604/103.01 |
| 5,460,610 | A | 10/1995 | Don | |
| 5,514,092 | A | 5/1996 | Forman et al. | |
| 5,599,307 | A * | 2/1997 | Bacher | A61F 2/82 604/101.05 |
| 5,662,609 | A * | 9/1997 | Slepian | A61L 24/0031 604/101.03 |
| 5,711,754 | A | 1/1998 | Miyata et al. | |
| 5,913,861 | A | 6/1999 | Trotta | |
| 6,148,222 | A * | 11/2000 | Ramsey, III | A61N 1/0517 600/373 |
| 6,485,500 | B1 * | 11/2002 | Kokish | A61M 25/104 604/101.01 |
| 6,488,653 | B1 | 12/2002 | Lombardo | |
| 7,060,051 | B2 * | 6/2006 | Palasis | A61L 29/085 604/101.01 |
| 7,077,836 | B2 * | 7/2006 | Lary | A61M 25/10 604/509 |
| 7,862,601 | B2 | 1/2011 | Sanati et al. | |
| 8,388,671 | B2 | 3/2013 | Letort | |
| 8,414,611 | B2 * | 4/2013 | Chalekian | A61F 2/954 606/192 |
| 9,302,081 | B2 | 4/2016 | Salerno | |
| 9,943,669 | B2 | 4/2018 | Salerno | |
| 2001/0001812 | A1 | 5/2001 | Valley et al. | |
| 2002/0010418 | A1 * | 1/2002 | Lary | A61M 25/10 604/101.04 |
| 2003/0120256 | A1 * | 6/2003 | Lary | A61M 25/00 604/509 |
| 2003/0181856 | A1 * | 9/2003 | Goldman | A61F 2/958 604/103.01 |
| 2004/0199155 | A1 * | 10/2004 | Mollenauer | A61B 18/08 606/27 |
| 2005/0033227 | A1 * | 2/2005 | Brodersen | A61M 25/0029 604/102.01 |
| 2005/0107738 | A1 * | 5/2005 | Slater | A61M 25/10 604/96.01 |
| 2005/0113798 | A1 * | 5/2005 | Slater | A61M 25/01 604/508 |
| 2005/0261722 | A1 | 11/2005 | Crocker et al. | |
| 2006/0135985 | A1 * | 6/2006 | Cox | A61F 2/07 606/194 |
| 2006/0271151 | A1 * | 11/2006 | McGarry | A61B 17/12045 623/1.11 |
| 2009/0018486 | A1 | 1/2009 | Goren et al. | |
| 2010/0280451 | A1 * | 11/2010 | Teeslink | A61B 17/12045 604/99.04 |
| 2013/0110081 | A1 * | 5/2013 | Roorda | A61B 17/12022 604/509 |
| 2016/0339213 | A1 * | 11/2016 | Martin | A61M 25/1002 |

OTHER PUBLICATIONS

PCT ISA Written Opinion (PCT Rule 43bis.1) for PCT/EP2007/063320 filed on Apr. 12, 2007 in the name of Mario Salerno.

PCT IPEA Written Opinion (PCT Rule 66) for PCT/EP20071063320 filed on Apr. 12, 2007 in the name of Mario Salerno.

PCT International Preliminary Report on Patentability for PCT/EP2007/063320 filed on Dec. 4, 2007 in the name Df Mario Salerno.

Nichols et al., "Importance of Balloon Size in Coronary Angioplasty", J. Am. Coll. Cardiol., 13: 1094-1100 (1989).

Kiousis et al., "Experimental Studies and Numerical Analysis of the Inflation and Interaction of Vascular Balloon aatheter-Stent Systems", Ann. Biomed_ Eng., 37: 315-330 (2009).

Product Catalog of PTCA Dilation Catheters of the Cordis company, 148 pages (2012).

Instructions for the Express® SD Renal Premounted Stent System of Boston Scientific, 8 pages. (2009).

Instructions for the Omnilink® 035 Biliary Stent System of Abbott, 11 pages. (Jan. 24, 2007).

* cited by examiner

ASSIST DEVICE FOR SCLEROSING TREATMENT OF VARICOSE VEINS

This application is a divisional application of application Ser. No. 15/052,470 filed Feb. 24, 2016 which is a divisional application of application Ser. No. 12/517,695, filed Jul. 8, 2009, which claims the priority of Application Serial No.PCT/EP2007/063320, filed Dec. 4, 2007 and Italian Patent Application Serial No. MI2006A002333, filed Dec. 5, 2006.

FIELD OF THE INVENTION

The present invention relates to an assist device for sclerosing treatment of varicose veins. In particular, the present invention concerns an intravascular catheter, which is introduced into the veins suffering from varices, so as to assist a local sclerosing treatment using a liquid drug or sclerosing foams.

BACKGROUND OF THE INVENTION

One of the most frequent pathologies that affects the venous system of the Western population is represented by the venous insufficiency, and nowadays it is estimated that more than 60% of the adult population suffers from this problem.

The most common manifestation of this pathology is varix. This term indicates the dilation, the tortuous course of the superficial veins, the valve insufficiency with a related reflux, whose appearance is mainly referable to intrinsic anomalies of the vein wall, high intraluminal pressure, structural and functional vein changes.

Although varicose veins constitute a benign pathology, they can be accompanied by two kinds of serious complications: ulceration and thrombophlebitis. The ulceration occurs usually near the ankle and, generally, in cases of particularly extended varices, while the thrombophlebitis consists of the presence of thrombi, real plugs constituted initially by platelets and fibrin, to which red corpuscles are added later inside the vein, together with an inflammatory response of the vein wall. The complication of the thrombophlebitis is pulmonary embolism, that expresses itself with clinical pictures of different seriousness, up to death.

The therapy for the varicose disease, proposed today, follows four kinds of approach: pharmacological, elastic compressive, surgical subdivided into classical or endovascular and sclerotherapeutic.

In particular, the endovascular surgery has been recently standing out, because of its less invasive character, and the sclerotherapy, that lives a new era with the arrival of the foams. The sclerotherapy consists of injecting into the varix a sclerosing substance which causes the lumen closure and consequently, disappearance of the varix, followed by application of an elastic compressive brace (stocking or bandage). This method is getting more and more attention from medicine.

Four variables must be taken into consideration, in order to make the sclerosis efficient:
1) the drug must have high destructive power on the endothelium and possibly also on the subendothelial structures and at the same time be gentle to other vasal and perivascular structures and further it should not have significant systemic side effects
2) it must get in contact with as much of endothelial surface as possible
3) the concentration of the drug must remain as stable as possible in the injection place and/or in the place of contact with the vein wall,
4) the contact time must be sufficient to determine the damage. At present, the sclerotherapy is commonly carried out by injecting a sclerosing drug in liquid form, or a so-called sclerosing foam, a preparation, in which the active substance having foaming capability is first subjected to a turbulence by energetic shaking, that creates micro bubbles (30-100 micron diameter) structured foam or mousse constituted substantially by gas, internally, and by foam active substance, that forms the outer surface of the bubble, for example of drug: sodium tetradecilsulphate or polydocanol.

The diluting effect due to the circulation can be considered a consequence on one hand positive, since it limits the risks of a progressive and uncontrolled sclerosis, on the other hand negative, because the dilution influences the sclerosis efficacy.

The sclerosis with foam or mousse has overcome successfully the dilution problem: the mousse (micro-bubbles of gas and drug) does not mix with a liquid, and, once injected into vein, it is capable of displacing the blood and coming in contact with venous endothelium more easily, improving the sclerosing effect (a better immediate and distant result appears from the literature). Therefore, it behaves as an almost solid substance and actually, it is a dynamic fluid aggregate of bubbles.

This has allowed reducing the dose of drug being used and its concentration (thus, we would expect a smaller number of complications, but actually the exact opposite effect appears from the literature: a larger number of side effects and new side effects).

Actually, it has been noted that the injected micro-bubbles get into the circulation and are subjected to the venous circulation effect, which is extremely variable at the lower limbs level, due to the system complexity, and moreover, it is difficult to predict its flow directions. Therefore, the micro-bubbles can reach the deep venous circulation, thrombosis of the deep veins, and inevitably, end up in the lung and the systemic circulation, thus causing side effects (headache, visual alterations, constriction in the chest), even potentially serious (stroke).

Consequently, in order to try to enhance the scleromousse methodology efficacy, some devices have been conceived and produced, substantially catheters, which are capable of better controlling the sclerosing foam location, the contact time of the drug with the vein wall, its effect and possible side effects.

A first device of this kind is a direct catheter, which is used for injecting the sclerosing foam at the desired point and along the whole venous axis, during the catheter distal end withdrawal. With this catheter, it is possible to control the place and the quantity of the injected drug (echo-sclerosis), however it is not possible to control a series of events: 1) the dilution caused by the blood flow that disperses the bubbles 2) the effective contact of the drug with the whole wall, for the same reason 3) the contact time, for the same reason 4) getting into the circulation, for the same reason.

Currently, other typologies of catheters are known: a two-way catheter with a distal balloon that allows to better control the sclerosing foam injected into the vessel through outlet holes, situated near the balloon, holes that allow sucking the foam out of the vessel through the same catheter afterwards. Another one, still with a distal balloon, but having many holes along the catheter axis, so as to distribute uniformly the drug in the part of the vein to be treated.

Also these two catheters are not completely free from some limits. The first device does not ensure a uniform concentration of the drug (foam) along the entire section of vessel to be sclerosed. The concentration decreases as one moves away from the balloon, that is from the outlet hole. Consequently, the varicose vein treated section will get in contact with a more and more diluted drug (foam), as one moves away from the outlet hole. It is confirmed by the fact that during the foam suction step, a mixture of foam/drug and blood is constantly recovered.

Moreover, because of the necessity to carefully inject quantities of foam not bigger than 6-10 cc, the initial volume of the varicose vein to be treated can influence even considerably the drug/volume ratio inside the vessel and in some cases jeopardize its therapeutic result.

In the second case, with more outlet holes, even if a more homogeneous concentration can be maintained along the whole section of the vein, and a given quantity of drug (for example 8 ml) must be used, standard concentrations of drug cannot be ensured in the section of the vein to be treated, for all kinds of varices.

Thus, all these devices, some more some less, along with the vessel subjected to a sclerosing therapy, constitute an "open system", that is a system under the influence of the venous circulation, resolve only partially the previously described problems.

In order to obviate such disadvantages, one must take into consideration the necessity to isolate the part of varix to be treated with a double balloon catheter, thus creating a "closed system", not exposed to the effect of the local venous circulation. Such a "closed system" is composed of the segment of varix under consideration, the catheter present therein, two balloons at the extremities, the blood contained in the isolated and static section of the vein.

The drug, in the form of mousse (stable and constant volume), is injected into such a "closed system", dislocates, in the small collateral vessels, the blood contained in the system, occupying the entire part of the vein being treated without any dilution.

The characteristic feature of this system is the location of the foam in a closed system, which consequently is not subjected to the local circulation effects, thus resolving the dilution problem.

However, although theoretically this system fulfills the conditions to be considered stable and thus efficient, also such solution has some limits.

Actually, the veins to be treated with the sclerosing foam can have variable dimensions and volume, that can range from a minimum of about 7-10 cm$^3$ to a maximum of 90-120 cm$^3$ and, since one cannot introduce as big quantity of sclerosing foam as desired, so as not to make its effect uncontrollable, for example having to use about 8 ml of foam, to satisfy the treatment of a section of vessel, whose volume varies from 10 cm$^3$ to 100 cm$^3$, it is noticed immediately that in the first case the foam concentration and the volumetric filling of the part of the vein to be treated is high (8:10=80%), while in the second case it is very low (8:100=8%).

This causes a high foam-volume concentration in the first case and a very low one in the second case, with obviously very different final results.

Therefore, disadvantageously, the two-balloon catheters defining a closed system do not allow treating efficaciously big dimensions blood vessels without introducing big quantities of medicine and consequently, risking to lose the control over the treatment.

Moreover, since it is necessary to inject into a closed system with two balloons at the ends, the syringe will require high operating pressure, so as to be able to dislodge the blood in the collateral vessels. This could cause a leakage of the micro-bubbles into the collateral circulation (perforating), before emptying the section of the part of blood, thus increasing the TVP risk.

SUMMARY OF THE INVENTION

The object of the present invention is to provide an assist device for sclerosing treatment of varicose veins, which is capable of resolving the above mentioned drawbacks of the known technique in an extremely simple, economic and particularly functional way.

Another object of the present invention is to provide an assist device for the sclerosing treatment of varicose veins, that defines a closed system, which can allow an efficient and standardized treatment of the varices using the sclerosing foams, ensuring an optimal foam-volume-surface of the vessel to be treated ratio.

A further object is to provide an assist device for the sclerosing treatment of varicose veins, that allows improving the sclerosing action of the sclerosing mousse, reducing at the same time possible side effects related to the foams.

A still further object is to provide an assist device for the sclerosing treatment of varicose veins, that allows using a low quantity of sclerosing drug, also for blood vessels of big dimensions.

Yet a further object is to provide an assist device for the sclerosing treatment of varicose veins, that allows using an action efficacy time, which is not affected by external agents capable of altering the sclerosis efficacy (closed system).

The above mentioned objects are obtained according to the present invention by a device (10) at least partially insertable into a blood vessel (20) for assisting a sclerosing treatment of varicose veins comprising a tubular element (11) having at least three ways (13, 14, 15), at least two (13, 14) of said at least three ways each being connected to at least one related inflatable balloon element (12, 12', 16) by at least one through hole (30, 31), and at least one remaining way (15) of said three ways (12, 14, 15) has at least one hole (32) for the passage of a sclerosing substance (17), for reaching a wall (18) of said blood vessel (20), wherein at least one (16) of said balloon elements (12, 12', 16) has an elongated shape extending toward at least another (12, 12') of said balloon elements and a volume in a range from 30% to 99% of the space inside said blood vessel (20), conveniently the at least one (16) of said balloon elements being interposed between the external surfaces of the outermost of said at least two balloon elements (12, 12'), so that said elongated balloon element (16), extending toward another balloon element, standardizes the residual volume to be filled with said sclerosing substance, independently from the dimensions of the vessel to be treated.

Other characteristics of the invention are pointed out in the dependent claims.

BRIEF DESCRIPTION OF THE DRAWINGS

The characteristics and advantages of an assist device for sclerosing treatment of varicose veins, according to the present invention will become clearer from the following description, given as a pure, not limiting example, with reference to the enclosed schematic drawings, in which.

BEST MODES OF CARRYING OUT THE INVENTION

Figure 1:
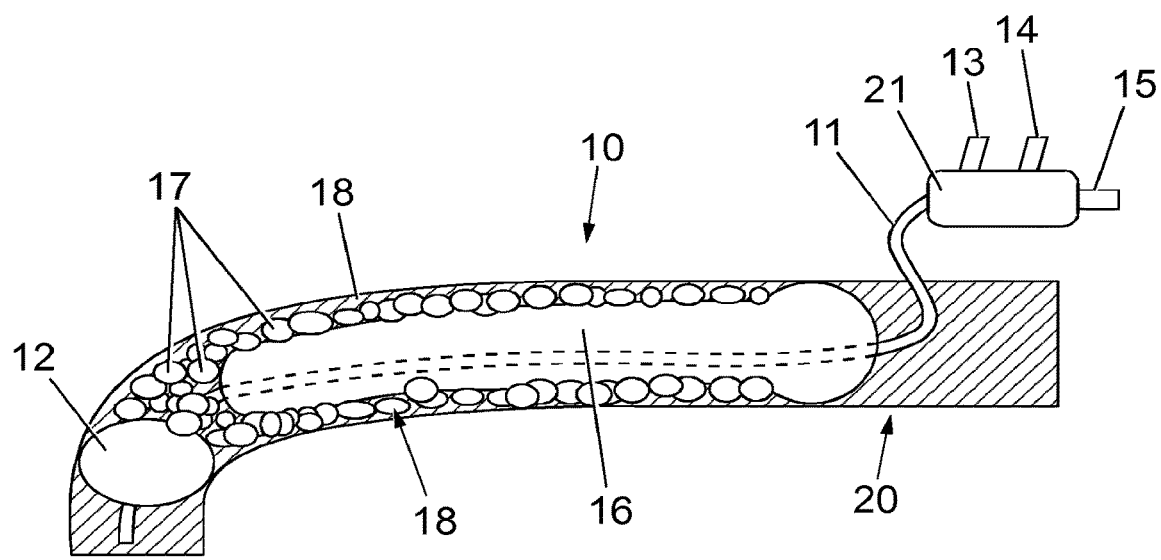
FIG. 1 shows an embodiment of an assist device for sclerosing treatment of varicose veins, according to the invention, during an in-operation step and inserted in a blood vessel.

With reference to the Figures, an embodiment of an assist device for sclerosing treatment of varicose veins, according to the invention is shown and indicated as a whole with reference numeral 10.

The shown device 10 is aimed at being partially inserted into a blood vessel 20 and includes a tubular member 11, having at least three ways 13, 14, 15.

The three ways 13, 14, 15 are independent one from another, and at least two of them 13, 14 are connected, each by related through holes 30 and 31, to at least one balloon element 12, 12' and 16.

Advantageously, the provided embodiments of the device proposed by the present invention include at least two balloon elements 12, 12' and 16.

Typically, at least two balloon elements 12, 12' and 16 are inflatable and reach their maximum expansion when a fluid, typically a liquid such as a normal saline solution, introduced into the related ways 13, 14 by an operator from outside, is conveyed into them through the above mentioned related through holes 30, 31.

Also the other at least a way 15 has at least one hole 32, in the region of which there is no element, so that a substance, typically in solution 17, inserted from outside into the related way 15, reaches the walls 18 of the blood vessel 20.

Such a substance 17 contains a drug, such as polydocanol, for the sclerotherapy, that can be either a solution, or advantageously, foam.

In order to facilitate the insertion of the related substances into the three ways 13, 14, 15, the device 10 includes also an adapter 21, in which the three ways can be reached separately and individually by an operator from outside.

According to an embodiment. at least one balloon element 16 of the at least two above mentioned balloon elements 12, 12' and 16 has preferably a non symmetrical spherical shape, which typically is elongated toward at least one other balloon element 12, 12', that usually has a spherical shape.

According to an embodiment, the elongated balloon 16 has a fixed longitudinal axis, that cannot be changed, and a transversal section, that can be changed, due to the inflation effect.

According to an embodiment of the invention, the inflated balloon element 16 occupies almost the whole space of the vessel interposed between the two of at least two balloon elements 12, 12' and 16, which are situated at the end of the device 10.

In this way, after having been inflated and dislocated the blood, the elongated balloon element 16 occupies between 30% and 99%, preferably between 60% and 80% of the inner space of the blood vessel 20 to be treated, interposed between the external surfaces of two of the at least two balloon elements 12, 12' and 16, which are situated at the end of the device 10.

Typically, since the elongated balloon 16 can change its dimension, not in longitudinal direction, but substantially only in the transversal one, that is, it can change its diameter due to the inflation, it is capable of changing, reducing its volume, the quantity of blood present in the part of vein to be sclerosed. Depending on the inflation degree, the balloon can empty the part of varix to be treated substantially (about 99%) or only partially 60-80%. Therefore, independently from the initial dimensions, diameter/volume, of the vessel to be treated, that can widely vary from 10 cc to 120 cc, and due to the volumetric modularity of the elongated balloon, interposed between at least two spherical balloon elements 12 and 12', it is possible to create always a standard residual volume of the blood vessel to be sclerosed. Typically, such residual volume of a vessel full of blood, will be restricted in the area comprised between A) the at least two spherical balloons 12 and 12';
B) the at least one elongated balloon 16, coaxial with the catheter and
C) the wall 18 of the blood vessel 20.

Advantageously, the drug is then injected in such residual volume. If the residual volume of the vein is standard, independently from the initial volume, the quantity of drug to be used must be always the same, independently from the vessel initial volume. The use of always the same quantity of drug in a closed system means standardization of the treatment.

According to this embodiment, the standardization is possible because all the negative variables can be controlled: 1) the dilution caused by the blood flow, 2) the contact time depending on the flow; 3) the contact with all the endothelium along its whole circumference; 4) the drug concentration in the residual volume for the reasons explained before.

Generally, the tubular element 11 is made of radiopaque polyurethane or Pebax, incompressible and flexible, while the balloon elements 12, 12' and 16 are made of latex, covered or not, with polytetrafluoroethylene (PTFE), of silicone, or other elastic material.

As already said beforehand, the assist device for sclerosing treatment of varicose veins, according to the invention, has at least two balloon elements 12, 12' and 16, at least one of which 16 is preferably extendable. Thus, according to preferential embodiments, there can be embodiments that include a number of balloon elements bigger than, equal to, but never smaller than two, as shown in FIGS. 1 and 2.

Figure 3:
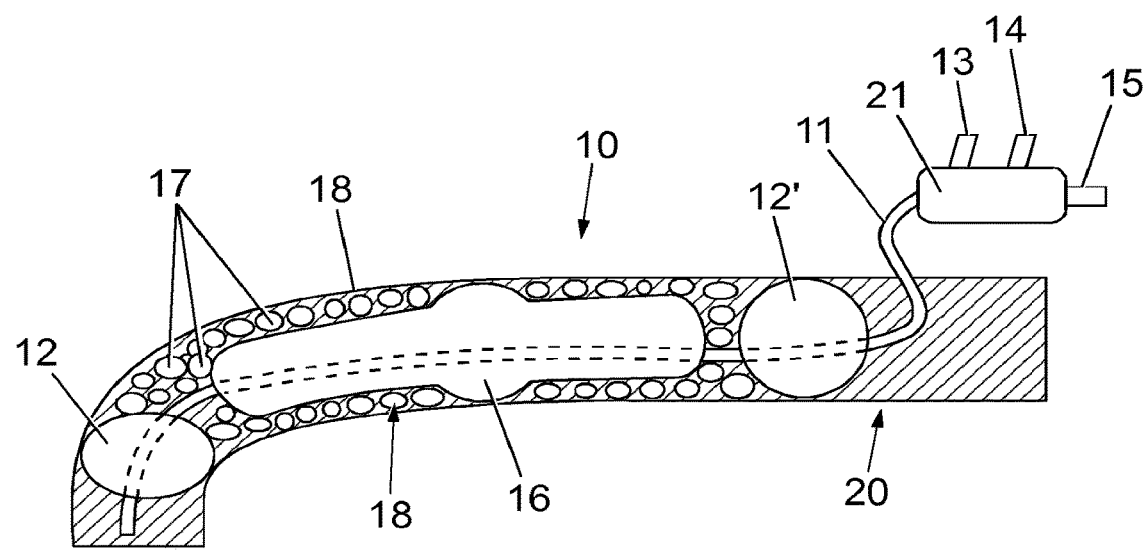
FIG. 3 shows another embodiment of an assist device for sclerosing treatment of varicose veins, according to the invention during an in-operation step and inserted in a blood vessel.
Figure 4:
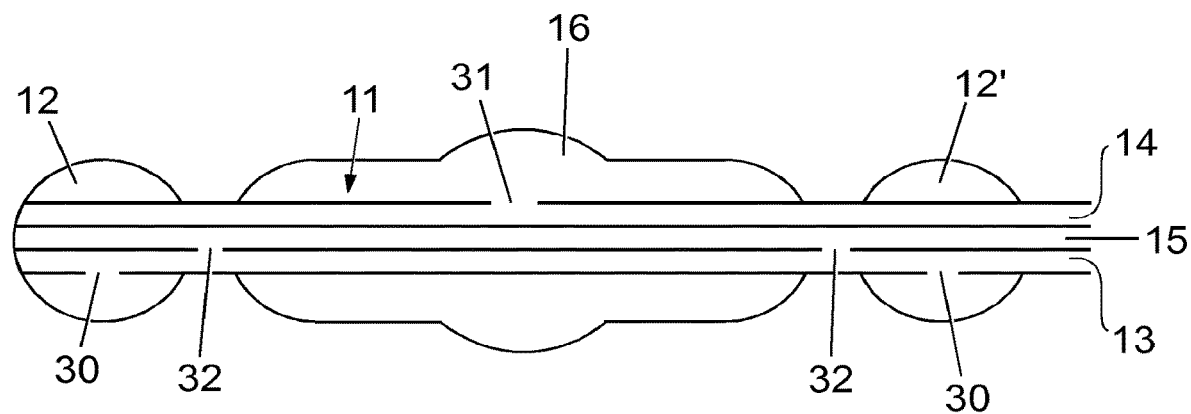
FIG. 4 is a schematic view, in vertical section, of a portion of the device of FIG. 3.

Otherwise, it is possible to have more, for example three balloon elements, as shown in FIG. 3.

Figure 2:
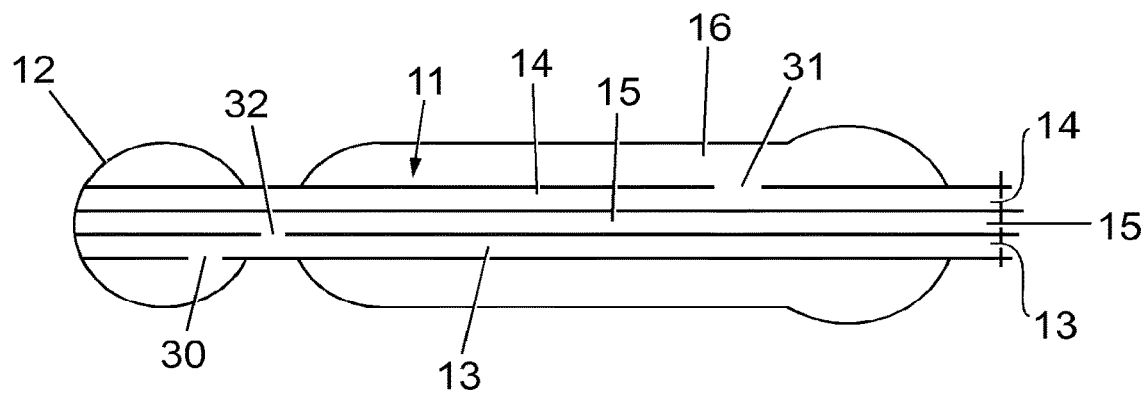
FIG. 2 is a schematic view, in vertical section, of a portion of the device of FIG. 1.

According to the embodiment with two balloon elements 12 and 16, shown in FIGS. 1 and 2, after having been inflated, the balloon element 16 occupies almost the whole space interposed between the latter and the remaining balloon element 12.

In particular, the inflated balloon element 16 occupies from 30% to 99%, preferably from 60% to 80%, of the inner space of the blood vessel 20 to be treated, interposed between the external surfaces of the two balloon elements 12, 16.

Consequently, according to this embodiment, the balloon element 16 has a non symmetrical shape, including a portion elongated toward said balloon element 12, which begins from an approximately spherical portion.

A contact between the wall 18 of the blood vessel 20 and the balloon element 16, in this example, occurs only in its spherical portion, which is located in a position opposite to the other balloon element 12.

According to an embodiment, the inflatable balloon element (16) includes an elongated portion which permits first the inflation of the spherical portion and after of the cylindrical portion extending toward said balloon element (12).

According to an embodiment, the balloon (16, 12, 12') of the device of the invention can be made of an (elastically) deformable material having different stiffness/wall density or of two or more materials having different elastic properties in order to permit sequential inflation and deflation of portions thereof. For example, when the balloon 16 is made of a single elastic material, it is possible to have the spherical portion of the balloon 16 with a lower thickness or material density than the elongated portion. In this way, the differential wall density/thickness of the material of the balloon 16 allows a sequential inflation and a subsequent deflation steps. In particular this embodiment enables the operator to inflate first the spherical part of the balloon 16 (which is thinner) and afterwards the elongated cylindrical part.

Typically, such effect of sequential expansion of the elongated balloon 16 could be obtained also by using two materials having different stiffness for the spherical part and the elongated cylindrical part, forming the balloon. Otherwise, the same effect could be achieved by an embodiment with a balloon molded with such shape, elongated with one of the two ends being spherical (FIGS. 1 and 2).

According to a further embodiment, there are more than two balloon elements and, as shown in FIG. 3, there can be for example three balloon elements 12, 12' and 16.

At least one balloon element 16 of these three balloon elements 12, 12' and 16 has an elongated form and preferably it is the one situated in a central position between the other two 12, 12'.

Typically, the balloon element 16 has an elongated form, is interposed between the two spherical balloons 12 and 12', placed externally and, once inflated, it occupies from 30% to 99%, preferably from 60% to 80%, of the inner space of the blood vessel 20 to be subjected to the sclerotherapeutic treatment.

According to this embodiment, the elongated balloon element 16 has a symmetric form with two external elongated portions extending, beginning from a central spherical portion, toward the remaining two balloon elements 12, 12'.

According to this embodiment, there can be a balloon 16 with elongated shape, as described above, such that it gets in touch with the wall 18 of the blood vessel 20 in its central portion, FIG. 3, and in this case, forming two closed systems, there are holes 32 in both said systems, or there can be a central balloon 16 with elongated shape, that does not get in touch with the wall 18 of the blood vessel 20 in any point.

Figure 5:
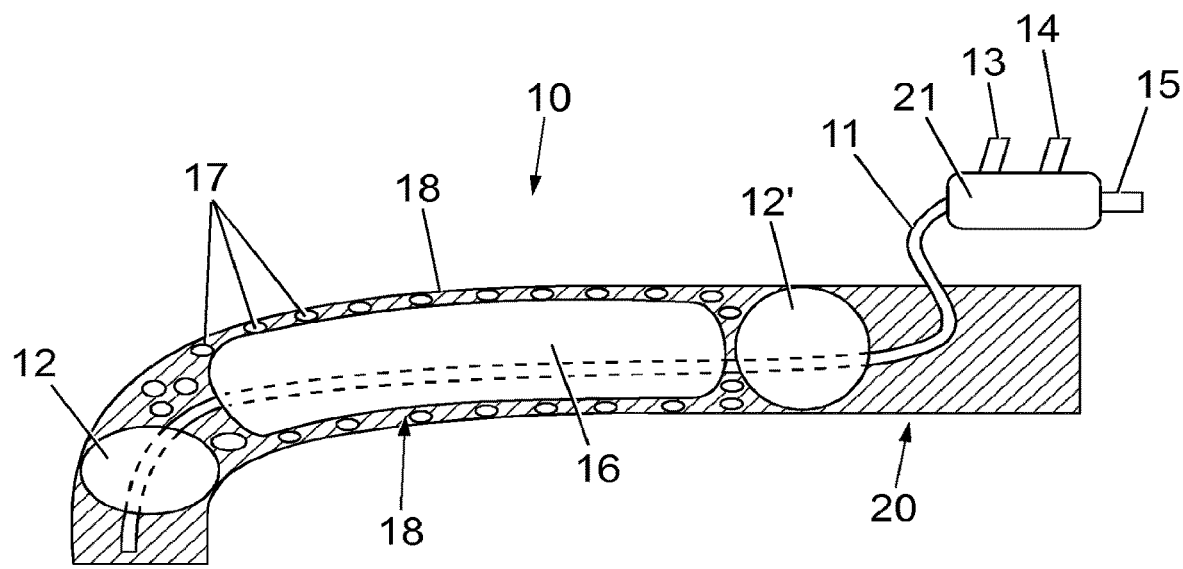
FIG. 5 shows a further embodiment of an assist device for sclerosing treatment of varicose veins, according to an in-operation step and inserted in a blood vessel.

In the last case, a single closed system is created, delimited by the remaining two lateral balloon elements 12 and 12', FIG. 5, and there can be even only one hole 32.

In this way, the same effects of the embodiment shown in FIGS. 1 and 2 with two balloon elements 12 and 15, are ensured.

In the just described embodiment with three balloon elements, taking the central one as the elongated element, being symmetrical, it is possible providing, without jeopardizing the device efficacy, a uniform wall density of the material, from which the device has been made, or only one material for the whole elongated balloon element 16.

Finally, the elongated balloon element 16 works typically in an autonomous way with respect to other remaining balloon elements.

This is allowed in all the embodiments by providing that one of the at least three ways 13, 14, 15, present in the device 10, is aimed, exclusively and independently from the remaining two, at supplying the elongated balloon 16.

The remaining ways of the at least three ways 13, 14, 15, will supply, always independently, the drug to the treated part of the vessel and the other balloon elements 12, 12'.

It is quite easy to understand the operation of the device proposed by the invention.

The device 10 belongs to the category of catheters for sclerosing treatments, which are capable of creating a closed and isolated system, in the area of the blood vessel subjected to the treatment.

Typically, in the operative conditions the catheter is inserted in a blood vessel to be treated. After the insertion, the balloon element 16 including an elongated portion, typically having a substantially cylindrical shape, is inflated by means of the passageway 14 and the hole 31 in order to substantially fill the vessel to be treated by dislocating the blood therein contained, independently from the starting diameter/dimension of said vessel. The next step comprises the inflation of the distal balloon 12 through the passageway 13 and the hole 30 in such a way to substantially occlude the system (closed system). After that, a sclerosing drug is injected by means of the passageway 15 and the hole 32 to substantially fill the residual space existing between the balloon 16 provided with the elongated portion and the second (distal) balloon 12. According to an embodiment, the elongated portion of the balloon 16 is partially deflated by means of the hole 31 and the passageway 14, during drug injection. By this operation it is created a depression which make easier to fill the space in the middle of the wall 18, the vessel 20, the balloon 16 and the second balloon 12.

Such closed system arrangement is indeed obtained by the presence of at least two inflatable balloons 12, 12' and 16, which, by expanding, isolate the volume of blood present therebetween from the blood circulation.

Further, according to an embodiment of the invention, at least one 16 of the said at least two spherical balloons 12, 12' and 16 has an elongated shape toward the at least another balloon element 12, 12'.

In this way, it occupies a volume in the range from 30% to 99% of the space of the blood vessel interposed between the two balloon elements of the at least two ones 12, 12' and 16, placed externally.

In this configuration, the free space remaining in such closed system is much smaller than the total volume of the blood vessel interposed between said at least two balloon elements, if such a devise was not present.

Moreover, such device is capable of reducing the above mentioned volume, so as to create a residual volume substantially standard, independently from the initial volume of the blood vessel to be treated. This effect is made possible due to the modularity of the elongated balloon element 16, which can be expanded by few millimeters, e.g. 3-4 mm, in the veins of small size, up to some tens, e.g. 20 mm and more, into the veins of big size.

In this way, by introducing even small quantities of drug 17, it is possible to achieve an optimal medicine-volume-endothelial surface of the vessel 20 to be treated ratio, also in the cases when vessels of big dimensions are to be treated.

Advantageously, the volumetric modularity of the balloon 16 allows reducing the inner volume, thus standardizing the residual volume, volume that is to be filled with the drug, independently from the initial diameter/volume of the vessel (e.g. 5-6 mm of diameter and 10-15 cc or 15-16 mm of diameter and 90-100 cc).

Without the use of the device according to the invention, the big vessels would require a big quantity of drug 17 to obtain the same r volume/drug ratio, with the risk of losing control over the treatment.

Advantageously, in the embodiments described in the present explanation, both the one with three balloon elements 12, 12' and 16, and the one with two elements 12 and 16, the elongated balloon 16, lateral or central, as the case may be, as already said before, works in an autonomous way with respect to the others, with the provision of an independent supply way for it.

The two remaining ways supply the remaining balloon elements 12, 12' and the drug 17 to the section of the vessel 20, subjected to the treatment.

In this way, the device with two balloon elements 12 and 16 has a balloon 12 dedicated supply way and another dedicated way for the elongated balloon 16, which will ensure, in operation, a sequential inflation-deflation due to its wall different density.

First, the spherical part will be inflated, and then the elongated part, so as to dislodge the blood and, after inflation of the remaining spherical balloon element 12, it will be afterwards slightly reduced in its elongated part.

By acting in this way, a facilitated supply of the drug 17 into the central chamber would be allowed, due to return vacuum effect, caused by the deflation of the elongated part of the balloon 16 (a small deflation, as the spherical-elongated balloon element 16 remains almost completely inflated). In case one decides to use a device with three balloons 12, 12' and 16, according to what said above, there will be one way for the central elongated cylindrical balloon 16, and another way for the two lateral spherical balloons 12 and 12'.

In this way, the elongated balloon element 16 could be inflated first, to dislodge the blood and afterwards deflated a little, prior to the contemporary inflation of the remaining spherical balloon elements 12 and 12'.

The so conceived system constitutes an efficient "closed system", which can be used in a "static or dynamic" way. Indeed, the described device according to the invention can operate in a static way, that is, one sets the device in place, then fills the chamber with the liquid or foam drug 17 and waits the necessary effect time with the catheter motionless in place (only afterwards the drug is sucked, the balloons are deflated and the device is removed).

Otherwise, the device can operate in a dynamic way, that is, one sets the device in place, then fills the chamber with the liquid medicine 17 or foam and proceeds by temporal intervals, subsequent to progressive removal of the device along the whole varicous venous axis to be treated. This solution constitutes a "dynamic closed system", because it is the chamber containing the drug that moves in the vessel, thus facilitating drug contact with the whole vessel to be treated. The system compares with the LASER o RADIOFREQUENCY treatments.

This therapy method uses catheters that carry heat energy, released into the vessel through the head (the catheter tip) during the withdrawal step, thus determining an endothelial damage with subsequent vessel sclerosis.

The "dynamic closed system" uses chemical energy (drug/sclerosing substance), that acts on the vein wall, determining the damage during the withdrawal step.

The "system is closed", not modifiable, with a constant concentration of drug in the chamber, and consequently on the vein wall.

It is the system stability that standardizes the therapy, optimizing it, for vessels of any dimension.

It is the correct and constant concentration of the drug on the vessel wall that determines the maximum effect.

Naturally, from the realization point of view, devices of various dimensions and proportions are provided.

Figure 6:
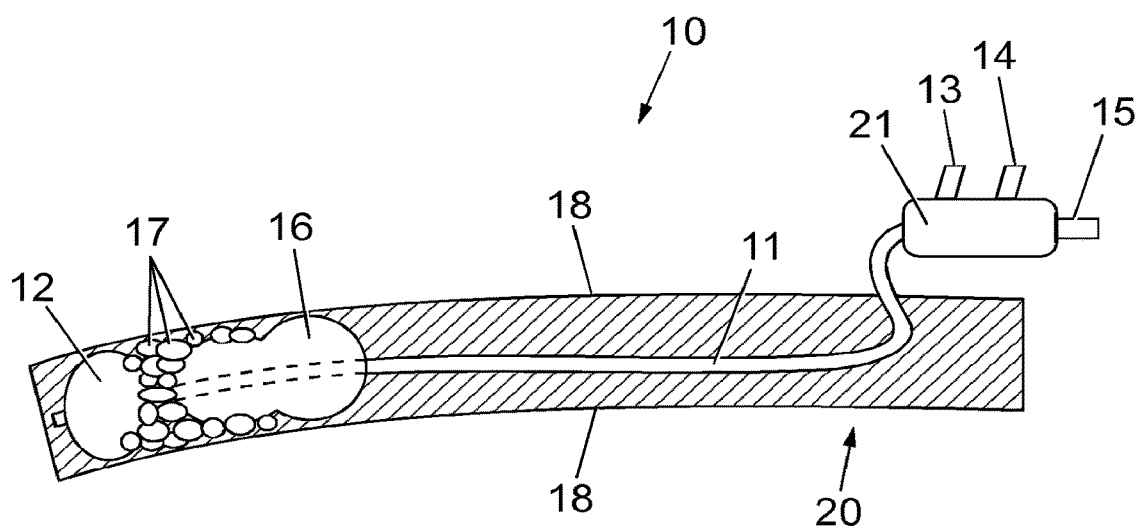
FIG. 6 shows a further embodiment of an assist device for sclerosing treatment of varicose veins, according to the invention, during an in-operation step and inserted in a blood vessel.

For a same length of the vein section to be treated, the device can have dimensions comparable to the vein section, for example FIG. 1, and in this case it will be used advantageously in "static" way, or, having smaller dimensions, FIG. 6, it can be used in "dynamic" way.

The invention claimed is:

1. A method for sclerosing treatment of a blood vessel having a wall, the method comprising the steps of:
   dislocating blood contained in an initial volume of the blood vessel to be treated by inserting a catheter in the blood vessel to be treated, the catheter comprising at least two inflatable balloons, said at least two balloons comprising:
   a first balloon including a spherical part and an elongated portion, and
   a second distal balloon;
   after insertion of the catheter, inflating the first balloon bby expanding the spherical part and then expanding the elongated portion, in order to substantially fill the blood vessel to be treated by dislocating the blood therein contained, independent of a starting diameter of the blood vessel;
   isolating a residual volume of the initial volume of the blood vessel to be treated from blood circulation, wherein said residual volume contacts an entire inner area of the wall of the blood vessel to be treated by inflating the second distal balloon, wherein the first balloon and the second distal balloon, by expanding, isolate the residual volume of the blood vessel to be treated, and wherein said residual volume is in contact with the blood vessel to be treated;
   injecting, by the catheter, a sclerosing drug in said residual volume;
   controlling a contact time between the sclerosing drug and the wall of the blood vessel to be treated by maintaining the first balloon and the second distal balloon in an inflated state.

2. The method according to claim 1, wherein the residual volume is independent from the initial volume of the blood vessel.

3. The method according to claim 2, wherein a quantity of sclerosing drug to be injected is independent from the initial volume of the blood vessel.

4. The method according to claim 1, wherein the residual volume is delimited by the first balloon, the elongated portion thereof, the second balloon and the wall of the blood vessel.

5. The method according to claim 1, wherein the steps of injecting and controlling comprise injecting the sclerosing drug to fill the residual volume between the first balloon and the distal balloon, wherein during drug injection the method partially deflates the elongated portion of the first balloon.

6. The method according to claim 5, wherein the operation of partially deflating creates a depression facilitating filling the residual volume.

\* \* \* \* \*